US006287693B1

(12) United States Patent
Savoir et al.

(10) Patent No.: US 6,287,693 B1
(45) Date of Patent: Sep. 11, 2001

(54) STABLE SHAPED PARTICLES OF CRYSTALLINE ORGANIC COMPOUNDS

(75) Inventors: John-Claude Savoir, Coyoacan; Juan Angeles, Nezahualcoyotl; Aurelio De Gyves, Coyoacan; Abraham Gomez, Nezahualcoyotl, all of (MX)

(73) Assignee: John Claude Savoir (MX)

( * ) Notice: Subject to any disclaimer, the term of this patent is extended or adjusted under 35 U.S.C. 154(b) by 0 days.

(21) Appl. No.: 09/030,388

(22) Filed: Feb. 25, 1998

(51) Int. Cl.$^7$ ........................................................ B32B 5/16
(52) U.S. Cl. ........................ 428/402; 424/408; 424/439; 424/451; 424/457; 424/458; 424/465; 424/469; 424/470; 424/489; 428/402.24
(58) Field of Search .................................. 428/357, 402, 428/402.24; 424/401, 408, 439, 451, 455, 457, 458, 465, 469, 470, 489, 459

(56) References Cited

U.S. PATENT DOCUMENTS

| 2,447,362 | 8/1948 | Pessel . | |
|---|---|---|---|
| 4,347,234 | * 8/1982 | Wahlig et al. | 424/15 |
| 4,447,426 | * 5/1984 | Wang et al. | 424/243 |
| 4,521,431 | 6/1985 | Crookes et al. . | |
| 4,584,366 | 4/1986 | Gerking et al. . | |
| 4,810,566 | 3/1989 | Kawakami et al. . | |
| 4,897,307 | 1/1990 | Beck et al. . | |
| 4,919,899 | 4/1990 | Herrmann et al. . | |
| 4,948,871 | 8/1990 | Fukuoka et al. . | |
| 4,996,222 | * 2/1991 | Carlin et al. | 514/400 |
| 5,069,910 | * 12/1991 | Kovacic et al. | 424/464 |
| 5,290,913 | 3/1994 | McAllister et al. . | |
| 5,360,478 | 11/1994 | Krukonis et al. . | |
| 5,391,810 | 2/1995 | Abe et al. . | |
| 5,409,505 | 4/1995 | Morita et al. . | |
| 5,512,303 | * 4/1996 | Garza Flores et al. | 424/489 |
| 5,558,678 | 9/1996 | Weger . | |
| 5,643,604 | * 7/1997 | Angeles Uribe et al. | 424/489 |
| 5,858,410 | * 1/1999 | Muller et al. | 424/489 |
| 5,874,063 | * 2/1999 | Briggner et al. | 424/45 |

FOREIGN PATENT DOCUMENTS

| 0054868 | 6/1982 | (EP) . |
|---|---|---|
| 0 364 944 | 4/1990 | (EP) . |
| 57099562 | 6/1992 | (EP) . |
| 0 508 969 | 10/1992 | (EP) . |
| 0 531 845 | 3/1993 | (EP) . |
| 0143832 | 8/1983 | (JP) . |
| WO91 19484 | 12/1991 | (WO) . |
| WO91/19484 | 12/1991 | (WO) . |
| WO99/43304 | 2/1999 | (WO) . |

OTHER PUBLICATIONS

Mueller et al., "Meling Behavior, Mechanical Properties and Fracture of Crystallized Polycarbonates" *LatinAmerican Journal of Metallurgy and Materials*, 50:130–141, 1985, No. 2.

Matsuda et al., "Physicochemical Characterization of Spray–Dried Phenylbutazone Polymorphs" *Journal of Pharmaceutical Sciences*, 73:173–179, 1984, No. 2.

Hancock et al., "Characteristics and Significance of the Amorphous State in Pharmaceutical Systems", *Pharmaceutical Sciences*, 86:1–12, 1997, No. 1.

Tang et al., "Effect of solvent vapor on optical properties of Pr4VOPc in polymethylmethacrylate", *J. Appl. Phys.*, 78:5884–5887, 1995, No. 10.

Frokjaer et al., "Application of differential scanning calorimetry to the determination of the solubility of a metastable drug", *Arch. Pharm. Chemi Sci. Ed.* 2:51–59, 1974.

Giron, "Thermal analysis and calorimetric methods in the characterisation of polymorphs and solvates", *Thermochimica Acta* 248:1–59, 1995.

Kawashima, "Characterization of Polymorphs of Tranilast Anhydrate and Tranilast Monohydrate When Crystallized by Two Solvent Change Spherical Crystallization Techniques", *Journal of Pharmaceutical Sciences*, 80:472–477, 1991, No. 5.

Ibrahim et al., "Polymorphism of Phenylbutazone: Properties and Compressional Behavior of Crystals", *Journal of Pharamceutical Sciences*, 66669–673, 1997, No. 5.

Yu, "Inferring Thermodynamic Stability Relationship of Polymorphs from Melting Data", *Journal of Pharmaceutical Sciences*, 84:966–974, No. 8.

Salole, "The physicochemical properties of oestradiol", *Journal of Pharmaceutical & Biomedical Analysis*, 5:635–648, No. 7.

Jerslev et al., "Organic solid–phase analysis", *Arch. Pharm. Chemi, Sci. Ed.* 9123–130, 1981.

Frokjaer et al., "Dissolution behavior involving simultaneous phase changes of metatable drugs", *Arch. Pharm. Sci. Ed.* 2:79–94, 1974.

Forni et al., "Solid state transitions and cap availability in surface solid dispersions of chloramphenicol stearate polymorphs", *Drug Development and Industrial Pharmacy*, 14:633–647, 1988, No. 5.

(List continued on next page.)

*Primary Examiner*—H. Thi Le
(74) *Attorney, Agent, or Firm*—Burns, Doane, Swecker & Mathis, L.L.P.

(57) ABSTRACT

The present invention provides storage stable, shaped particles of allotropic organic compounds. The particles of the present invention can be shaped according to the desired application. Preferred shapes of such particles are microspheres, particularly those having diameters of about 1 to about 1,000 microns. The stable shaped particles of the present invention are particularly well-suited to the fabrication of pharmaceutical formulations, particularly where sustained release and uniform bioavailability are desired. The storage stable particles are formed by a solid state crystallization of allotropic organic compounds. The solid state crystallization process of the present invention affords a means for achieving a storage stable crystalline form of said allotropic compound without loss or deterioration of the original particle dimensions.

11 Claims, No Drawings

OTHER PUBLICATIONS

Thakkar et al., "Miscellar Solubilization of Testosterone III: Dissolution Behavior of Testosterone in Aqueous Solutions of Selected Surfactants", *Journal of Pharmaceutical Sciences*, 58:68–71, 1969, No. 1.

Haleblian, "Isolation and Characterization of Some Solid Phases of Fluprednisolone", *Journal of Pharmaceutical Sciences*, 60:1485–1488, No. 10.

Yang et al., "Polymorphism in Sulfonamides", *Journal of Pharmaceutical Sciences*, 61:27–40, 1972, No. 1.

Muramatsu et al., "Thermodynamic Relationship between alpha– and beta–Forms of Crystalline Progesterone", 68:175–176, 1979, No. 2.

Pfeiffer et al., "Crystal Pseudopolymorphism of Cephaloglycin and Cephalexin", *Journal of Pharmaceutical Sciences*, 59:1809–1814, 1970, No. 12.

JP 57 0099562 A 21 Jun. 1982 Abstract) (Patent Abstracts of Japan, vol. 6, No. 186 (C–126) Sep. 22, 1982 (Abstract).

JP 9227558 A (Abstract) (Database WPI, Week 9748, Derwent Publications Ltd., London, GB; AN 97–516220 XP002107738) Sep. 2, 1997.

Database WPI, Week 9748, Derwent Publications Ltd., London, GB, AN 97–516220, XP–002107738 (Abstract).

* cited by examiner

STABLE SHAPED PARTICLES OF CRYSTALLINE ORGANIC COMPOUNDS

BACKGROUND OF THE INVENTION

It is well known that many substances are prone to crystallize in different manners, depending on the conditions under which they are crystallized. Different crystalline structures resulting from crystallization of a particular substance are called polymorphs or pseudopolymorphs. It is also known that, when they are melted and cooled rapidly below their melting point, i.e. melt-congealed, the atoms or molecules forming most substances need some time to arrange themselves in the order most natural for the environment in which they are placed. Accordingly, they remain in unstable amorphous or semiamorphous states or organize into metastable polymorphs.

Metastable polymorphs may be enantiotropic, which is a property of certain substances meaning that they can exist in more than one crystal form (Giron, Thermal Analysis and Calorimetric Method in the Characterization of Polymorphs and Solvates, Thermochimica Acta, 248 (1995) 1–59; Parker, Dictionary of Scientific and Technical Terms, McGraw Hill, Inc., 1984, 541; Hancock et al., Characteristics and Significance of the Amorphous State in Pharmaceutical Systems, J. Pharm. Sci., Vol 86, No. 1, 1997, 1–12). Often, there is a relation between the various crystal forms or habit of an enantiotropic substance such that one form is stable above the transition-point temperature and the other is stable below it. Consequently, the crystal habit is dynamic and reversible depending on ambient conditions.

Metastable polymorphs often transform over time into more stable structures. This natural crystallization process is called "aging", and occurs over time without human intervention. This natural "aging" process is often lengthy and unpredictable, and therefore is costly and potentially dangerous, particularly in the manufacture of pharmaceuticals. The unpredictability arises since the aging process largely depends on environmental factors. Yu, "Inferring Thermodynamic Stability Relationship of Polymorphs from Melting Data", J. Pharm. Sci., Vol 84, No. 8, 966–974 (1995).

Nevertheless, stable, crystallized substances are generally required for optimum and reliable bioactivity and bioavailability. If metastable particles, for example, microspheres or pellets, are placed in an aqueous medium before full crystallization occurs, deformation of particle shape or even complete destruction of the particles can occur in a matter of hours.

Furthermore, different polymorphs of a particular substance will have different dissolution rates, resulting in a lack of stability and loss of uniformity between different batches of the same drug. For example, Haleblian et al report differences in dissolution rates between polymorphs of fluprednisolone. Haleblian et al. "Isolation and Characterization of Some Solid Phases of Fluorprednisolone", J. Pharm. Sci., Vol. 60, No. 10, 1485–1488 (1971).

For pharmaceutical applications, it is particularly important to achieve stable crystallization, because administration of a therapeutic compound often requires suspension in an aqueous solution suitable for injection. Also, even if the compound is not first suspended in an aqueous medium, when it is administered to the patient it is subjected to biological fluids that are water based. The same is true for pellets and implants that are placed in the body through a surgical or other procedure. To assure the physical integrity of the shaped particles and uniform release of the active agent, it is necessary to assure full crystallization prior to administration.

Some workers have attempted to improve the stability of therapeutic compounds by inducing crystallization. For instance, Matsuda et al. suggest modifying crystalline structures using a temperature controlled dispersion drying method. Matsuda et al. "Physicochemical Characterization of Sprayed-Dried Phenylbutazone Polymorphs", J. Pharm. Sci., Vol 73, No. 2, 73–179 (1984).

However, because dissolution of a solid is also related to surface erosion, the shape and size of the therapeutic particles must also be considered in addition to solubility. Carstensen, "Pharmaceutical Principles of Solids and Solid Dosage Forms", Wiley Interscience, 63–65, (1977). Thus, when a pharmaceutical compound is administered as a solid or suspension, the preservation of particular shape and size becomes an important factor for assuring the control and reproducibility of bioavailability and biodynamics.

With this in mind, Kawashima et al. proposed a method of spherical crystallization of Tranilast through the use of two mutually insoluble solvents, and conversion of the resulting polymorphs by means of heat. Rawashima et al., "Characterization of Polymorphs of Tranilast Anhydrate and Tranilast Monohydrate When Crystallized by Two Solvent Change Spherical Crystallization Techniques" in J. Pharm. Sci., Vol 80, No. 5, 472–477 (1981).

It has also been reported that the natural process of aging can be accelerated through heating. Ibrahim et al., "Polymorphism of Phenylbutazone: Properties and Compressional Behavior of Crystals" in J. Pharm. Sci., Vol 66, No. 5, 669–673 (1977); Hancock et al., Characteristics and Significance of the Amorphous State in Pharmaceutical Systems, J. Pharm. Sci., Vol 86, No. 1, 1–12 (1997). In some cases, however, the heat required is such that the integrity or shape of the substance is compromised. In several cases where heat has been used, reproducibility of results, stability, and hence control of crystal size within particles has been difficult or even impossible to achieve.

In addition, in some cases the most stable polymorph of a particular substance is a hydrate, rendering it impossible to reach the desired polymorph by means of heat due to resulting dehydration. Furthermore, heating is rarely appropriate for stable crystallization in the case of mixtures. Thus, the process of heat as a method for obtaining stable polymorphs, though superior to the aging process, has significant limitations.

Other workers have studied the use of solvent vapors to induce crystallization of polymeric species. Such efforts include putative crystallization and change of the mechanical properties of polymeric compounds, as described in U.S. Pat. No. 4,897,307. See also Müller, A. J. et al., "Melting behavior, mechanical properties and fracture of crystallized polycarbonates" in Latinoamericana de Metalurgia y Materiales, 5 (2), 130–141 (1985); and Tang, F. et al., "Effect of Solvent Vapor on Optical Properties of Pr/sub 4VOPe in polymethylmethacrylates", in Journal of Applied Physics, 78 (10), 5884–7 (1995).

Tang et al. used organic solvent vapors to transform a polymer matrix, Pr4VOPc dye (Vanadyl Phtalocyanine having 4 propyl substituents) from glassy phase I to crystallized phase II. Müller and Paredes describe the crystallization of polycarbonate polymers in terms of the incorporation of solvents or plasticizers into the amorphous state. To the knowledge of the present inventors, such an approach has not been used to form stable crystals of melt-congealed organic compounds and mixtures.

SUMMARY OF THE INVENTION

The present invention provides reproducible, stable particles of crystalline organic compounds. The stable particles of crystalline organic compounds of the present invention might be homogeneous particles of a singular organic compound, or they might be mixtures of two or more organic compounds. The stable particles of the present invention retain a constant shape and size during prolonged storage, such as in an aqueous suspension. Such stable particles can be fabricated to a uniform size and shape, and will retain said size and shape despite long term storage; and thus, are particularly advantageous in pharmaceutical formulations. The present invention further provides a method for obtaining such reproducible, stable particles. The method involves exposing the above shaped particles, wherein the one or more organic compounds is in a crystalline, amorphous, or some metastable form, to an atmosphere saturated with solvent vapors. The solvents are comprised of one or more liquids in which at least one or more of the organic compounds is soluble.

The method of the present invention affords several advantages. It is applicable to substances where the most stable polymorph is a hydrate, because it does not drive off water molecules and thereby allows the incorporation of water molecules into the crystalline web during formation. It is applicable to thermolabile substances, since high temperatures are avoided. And it allows stable structure formation involving a mixture of substances, which, with the exception of the eutectic mixture-composition, can not be attained by means of heat.

More particularly, the present invention involves a method of crystallizing or recrystallizing an amorphous or metastable crystalline organic compound or mixture. The method comprises the steps of (i) exposing said compound or mixture to an atmosphere saturated with the vapors of one or more liquids, at least one of which must be a solvent for said compound or mixture, for a time sufficient for transforming the metastable compound or mixture to a stable, crystallized compound or mixture; and (ii) recovering the stable, crystallized compound or mixture for storage or use.

The method may be performed using any enclosure where the volume, temperature, and atmospheric content and pressure can be manipulated. The chamber is capable of containing an atmosphere saturated with the desired solvent vapors. The point of saturation is reached when the vapors fill the chamber without causing condensation on the surfaces of the chamber or the particles.

Preferably the particles are formed into a shaped particle, such as a microsphere, pellet or implant form. Particles configured to have uniform and reproducible surface area are especially preferred. This can be effected by melt-congealing. Further, the shaped particles are preferably configured into a uniform particle size or range of sizes. To this end, the methods described in U.S. Pat. Nos. 5,633,014, 5,643,604, and 5,360,616 can be used, which are herein incorporated by reference. Alternatively, any suitable method that results in a metastable crystalline conglomeration can be used. Where the method involves crystallization of a mixture, the mixture may be eutectic or noneutectic.

The particles are placed in the chamber or other suitable enclosure using any suitable means such that they are exposed to solvent vapors, but not immersed in or otherwise contacting liquid solvent. The particles are stationary or mobilized within the chamber.

The time period necessary for effecting crystallization in accordance with the present method will vary depending on various physicochemical properties consistent with established principles. For example, the optimal time of exposure will vary depending on the shape and size of the particle, the chemical makeup of the particle, the form of the solid state of the particle (i.e., amorphous, metastable crystalline), the type and concentration of solvent used, and the temperature of the treatment. Generally, a range of several seconds to 48 hours is applied, or more preferably, 1 to 36 hours. Previous partial crystallization of particles does not appear to modify these time ranges. Optimization of the time of exposure will vary depending on the solvent system used, the organic compound(s) to be crystallized, and other variables, and is within the skill of one of ordinary skill in the art. As shown below, a 24 hour exposure time will commonly be effective.

One advantage of the present invention is that it is applicable to thermolabile substances because high temperatures may be avoided. Thus, the applicable temperature range is broadly defined and dependent on the particular compound. Generally, the temperature of the vapor atmosphere is sufficient to obtain vaporization of the solvent, but below the melting point of the particles.

The solvent or solvents used in the method of the present invention can be any agent classified as a solvent for the organic compound(s) of interest. As will be appreciated by any ordinarily skilled worker in the art, the selection of solvent will depend on the compound(s) sought to be stabilized. Exemplary solvents are conventional laboratory liquid solvents such as water, alkanes, alkenes, alcohols, ketones, aldehydes, ethers, esters, various acids including mineral acids, carboxylic acids and the like, bases, and mixtures thereof. Some specific exemplary solvents are methanol, ethanol, propanol, acetone, acetic acid, hydrochloric acid, tetrahydrofuran, ether and mixed ethers, pentane, hexane, heptane, octane, toluene, xylene, and benzene. Water is an especially useful component of a solvent/liquid mixture of the present invention, particularly where the most stable polymorph of a substance is a hydrate. Generally, solvents suitable for conventional liquid recrystallization of the compound of interest are suitable as a solvent in the present method.

The compound(s) of the stable particles of the present invention include any organic compound capable of existing as a crystalline solid at standard temperature and pressure. A preferred embodiment of the present invention is that wherein the particles are comprised of one or more organic compound(s) capable of forming into a stable crystalline solid. Preferably, the stable crystalline solid is a lattice of discrete organic molecules, i.e., non-polymeric.

Also preferred are organic compounds having some pharmacological or therapeutic activity. Still more preferred are such pharmacological compounds susceptible to the formation of polymorphs. Preferred embodiments further include particles comprised of a steroid or sterol, such as estrogen, 17β-estradiol, testerone, progesterone, cholesterol, or mixtures thereof. These mixtures can also include Oxatomide/Cholesterol, Niphedipine/Cholesterol, Astemizol/Cholesterol, which have non-steroidal components. Stable shaped particles of other organic compounds are also provided by the present invention, e.g., Cisapride, Oxatomide.

Because the method of the present invention results in significant stabilization of particles of amorphous or metastable crystalline organic compounds, the particles of the present invention can be stored in liquid suspension, such as aqueous medium, or administered directly to a patient. Because the present invention provides stable forms of existing pharmacological agents, it will be understood by those skilled in the art that the particles of the present invention can be used in accordance with conventional practice in analogous formulations, e.g., the parenteral administration of microspheres, administration of pharmacological agents via implants, etc.

DETAILED DESCRIPTION OF THE INVENTION

All publications and patent applications referenced herein are incorporated by reference to the same extent as if each individual publication or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The present invention provides stable shaped particles of one or more allotropic molecular organic compounds. Allotropic organic compounds are those capable of assuming two or more distinct physical forms (e.g., assuming different crystalline forms or an amorphous versus a crystalline form). Such allotropic species are also referred to as polymorphs or polymorphic species.

The formulations comprising storage stable, shaped particles of the present invention optionally further comprise pharmaceutically acceptable excipients, stabilizers, and buffers as are commonly known among those in the pharmaceutical arts.

These stable shaped particles possess an advantageous combination of physicochemical properties. First, the particles are configured into desired shapes by means that might not result in the most stable crystalline form of the constituent organic compound. The particles are then subjected to a solid state crystallization process that results in the organic compound assuming the most stable crystalline structure, and facilitates the retention of the size and shape of the original particle. The resultant product is a particularly configured particle comprised of one or more molecular organic compounds, each having a uniform crystalline character and possessed of a high degree of storage stability.

The combination of the uniformity of size and shape of the particle and the uniformity and stability of the crystalline structure of the constituent organic compound lends particular predictability and consistent bioavailability and associated biodynamics.

More particularly, the particles are pre-fabricated to desired specifications, e.g., microspheres of particular size and shape. The particles are then subjected to a solid state crystallization process that stabilizes the compounds of the particles without loss of the pre-fabricated size and shape. The resulting particles have greater uniformity of size and shape, more uniform and predictable dissolution profiles, and greater storage stability in various forms, e.g., in liquid suspension such as aqueous media or other storage liquid, as lyophilized solid, or alone as a powder or dry solid. By storage stable is meant the particles have improved shelf life without loss of the desired uniform size and shape of the particles, per se. That is, if the desired particle shape is a microsphere, the particles will retain a spherical shape of constant size over periods exceeding several years.

As used herein, storage stable refers to retention of the original size and shape of the particle, as well as the pharmacological activity of the active agent over a period of at least one month.

The present invention also involves a method of crystallizing shaped particles of a metastable compound or mixture of compounds without dissolution of the particle and attendant loss of the desired shape. The crystallization process is effected by exposing said particles to a controlled atmosphere saturated with the vapors of a solvent or solvents. The atmosphere is optionally modified in other respects, e.g., pressure, temperature, inert gases, etc. Preferably, the controlled atmosphere is saturated with a solvent vapor but not so much as to effect condensation of said solvent.

More particularly, the method of the present invention involves effecting crystallization of an amorphous or metastable organic compound in a shaped particle without alteration of the dimensions (e.g., size and shape) of said particle comprising: (i) exposing said shaped particle to an atmosphere saturated with the vapor of a liquid, said liquid being a solvent for said organic compound; and (ii) recovering said shaped particle wherein said organic compound is of a uniform crystalline structure.

Alternatively stated, the method involves effecting a solid state crystallization of a molecular organic compound in a particle of definite size and shape comprising: (i) exposing said particle to an atmosphere saturated with a solvent for said organic compound; and (ii) recovering said particle, wherein said organic compound in said recovered particle is of a uniform crystalline structure, and said recovered particle has retained said size and shape. Retaining the size and shape of the particle is meant to include minor variations in the dimensions of the particle, e.g., no more than about 15%; and preferably, no more than about 10%.

The present invention provides a means for fabricating particles of desired dimension without regard to the resulting allotropic form of the organic compound. After the particle is fabricated into the desired shape and size, the solid state crystallization can be effected to crystallize the organic compound into a storage stable solid state of uniform crystal structure. Moreover, the solid state crystallization of the present invention can be effected on particles comprised of more than one allotropic organic compound.

Preferably, the shaped particle is a microsphere; and, as a result of the present process, the organic compound(s) of the microsphere are ordered into a single, homogeneous crystalline form without any deterioration in the size or shape of the microsphere.

For purposes of the present invention, the term "crystallization" refers to a process by which the most stable polymorph of a particular substance is achieved. Recrystallization refers to a process similar to crystallization except that the organic compound of the particle, rather than being amorphous, was initially only partially crystalline, of a mixed crystalline habit, or crystalline, but of a less stable crystalline form. Unless indicated otherwise, the term crystallization includes recrystallization.

The term "solid state crystallization" refers to a crystallization process that is effected without macroscopic dissolution of the compound being crystallized. As used herein, solid state crystallization includes a crystallization process wherein an organic compound within a shaped particle is crystallized or rescrystallized by exposure to a solvent vapor without loss or alteration of the shape or size of the particle. It will be appreciated by those skilled in the art that while subtle intermolecular changes will be effected by such crystallization (e.g., creation or rearrangement of crystal lattice structure), the microscopic and/or macroscopic dimensions of the particle will not be appreciably altered.

The term "saturated" when used in reference to the atmosphere wherein the crystallization is conducted means that the atmosphere within the chamber or enclosure used to hold the solvent vapors contains the maximum quantity of said solvent in the vapor phase without effecting visible condensation on surfaces within the chamber. Condensation does not include microscopic condensation on the surface of the particles that does not affect their shape.

The term "solvent" refers to a liquid at standard temperature and pressure, and one capable of solubilizing an appreciable amount of a specified solid solute. The solid solute will be a particular organic compound. Solids vary from 0–100% in their degree of solubility. See, e.g., "Solubility Parameters of Organic Compounds", CRC Handbook of Chemistry and Physics, 62d ed., C-699, CRC Press; N. Irving Sax and Richard J. Lewis, Sr., Hawley's Condensed Chemical Dictionary, $11^{th}$ ed., 1079 (1987). For purposes of the present invention, a liquid will be a considered a solvent with respect to a particular solid solute provided the solute is at least 10% soluble in said liquid.

The term "particle" refers to a discrete collection of a plurality of molecules of one or more organic compounds. As used herein, a particle may be an ordered collection (e.g., crystalline) or disordered collection (e.g., amorphous) of molecules, or any combination thereof. The term embraces, among other things, microscopic as well as macroscopic particles such as powders, microspheres, pellets, implants, and the like.

Preferably, particles are made of microspheres. The preferred microspheres of the present invention range in size from 1 micron to 1 millimeter, more preferably 1 to 500 microns, and most preferably in the range of 1 to 100 microns, particularly for human use. When the particles are in pellet form, such particles are normally but not necessarily cylindrical with lengths of 1000 to 5000 microns and diameter of 500 to 1000 microns. These particles can have important applications for veterinary use, and are not injected but deposited under the skin.

The size and shape of the particle will depend on the intended application and the constituent organic compound (s). For example, microsphere size is chosen for practical reasons, i.e. a size appropriate for administration using a hypodermic needle or for assuring a desired rate of dissolution.

The term "molecular organic compound" refers to an organic compound existing as stable discrete molecules (i.e., non-polymeric) and when combined with a plurality of identical molecules is capable of assuming one or more ordered crystalline structures. Thus, a molecular organic compound is meant to distinguish from a polymeric species.

The term "metastable" means a pseudoequilibrium state of a solid substance where the content of free energy is higher than that contained in the equilibrium state. For our particular purposes, a "stable" substance or particle has a crystalline structure whose shape remains unchanged in a standard ambient environment, e.g. in air having varying levels of moisture, for an extended period of time. However, it should be understood that "stable" does not indicate infinite stability, but means sufficiently stable such that the particles remain sufficiently stable for the preservation of their crystalline characteristics during storage and up to their application and use and additionally, after they have been administered to a subject, up to their total dissolution.

The present invention also encompasses stable microspheres achieved using the present method. Such microspheres preferably contain a compound having pharmaceutical applications. The microspheres and pellets of the present invention are useful in human, as well as animal, therapeutic regimens.

For instance, there is currently a need for compositions that accomplish the sustained release of steroid growth promoters in food animals to promote the growth of such animals. The amount of growth hormone administered to an animal would depend on the particular animal species, hormone, length of treatment, age of animal, and amount of growth promotion desired. Other considerations to be made in the use of hormonal compositions in the treatment of animals are discussed in U.S. Pat. No. 5,643,595, which is herein incorporated by reference. The particles of the present invention can be particularly configured for optimal delivery by injection by varying the particle size.

As discussed above, the microspheres of the present invention are stable in aqueous fluids, and are thus amenable to parenteral injection. Modes of administration include but are not limited to intra-venous (IV), intra-arterial (IA), intra-muscular (IM), intra-dermal, sub-cutaneous, intra-articular, cerebro-spinal, epi-dural, intra-peritoneal, etc. In addition, the compounds of the present invention can be administered via an oral route, either as an aqueous suspension or a lyophilized product. Other routes of administration are also acceptable, including topical application, into the eye, or via inhalation in the form of droplets or mist.

The dosage form according to the present invention may take the form of a microsphere powder in vials/ampoules, ready to be prepared as suspensions, or take the form of ready-prepared suspensions, packaged into injectable ampoules or directly into syringes, ready to be administered in human or veterinary medicine. The suspension medium may be water, a saline solution, an oil, containing buffers, surfactants, preservatives, commonly used by pharmacotechnicians for preparing injectable substances or any other substance or combination which does not threaten the physical and chemical integrity of the substances in suspension and which is suitable for the organism which will receive it. If it is desired to avoid a sudden initial increase in the level of active ingredient in the internal medium of the receiving organism, it will be preferable in the case of ready-for-use suspensions to use liquid vectors in which said active ingredients are practically insoluble. In the case of active substances partially soluble in the lukewarm liquid vector but insoluble at cold temperature, it is preferable, from the pharmacological point of view, to avoid the formation of precipitates (called "caking" effect) by preparing formulations in the form of separate microsphere powder and liquid vector which will be mixed only at the time of injection.

In veterinary applications, where the duration of the desired effect may be very long (for example the lactation period of the adult female), diameters of a few hundreds of microns may be used. If it is desired to limit the diameter of injection syringe needles for the comfort of the patient, the diameter of the microspheres should be limited to 300 microns and more preferably to 100 microns. In contrast, for very short durations of effect (for example circadians), the diameter of a microsphere may be reduced to 5 microns.

For most applications in human medicine (duration of action of the active ingredient between a circadian cycle and a menstrual cycle), it is preferable to use microspheres whose diameter is between 5 and 100 microns, depending on the combinations of active substances/carrier substances.

A separation of microspheres according to their diameter may be performed during the manufacturing process using known processes: for example, by cyclonic separators, by sieving using air suction or by sieving in aqueous medium. In practice, it is sufficient if more than 70% of the microspheres have diameters of between 70% and 130% of a specified diameter. If necessary, the ideal dissolution curve, determined by the proposed application, may be approached by mixing batches with suitable different diameters. Moreover, particles which do not comply with the specifications may be recycled.

The mechanism by which substances in a solid state crystallize in the presence of vapors containing at least one solvent has not yet been established. The crystallization process may well conform, as regards the effect of the solvents, to the traditional principles that apply in saturated solutions and in molecular mobility. It is possible that some molecular rotational or transference movement occurs, which seems to depend on the particular type of solvent used and to the temperature of vaporization. Hancock et al., "Characteristics and Significance of the Amorphous State in Pharmaceutical Systems", J. Pharm. Sci., Vol 86, No. 1, 1–12 (1997). It is clear however that the temperatures at which the crystallization is obtained are well below vitreous transition temperatures and are in fact only in accordance with that required for the solvents' vapor pressure.

Without wishing to be bound by any theory, we contemplate that the vapor molecules of the solvent or solvents might form microcondensations and minute accumulations of solvent on the surface of the particles to be crystallized, thus bringing sufficient energy for the surface molecules of the solid particles to form organized structures (e.g., crystalline domains).

By the same token, if present in the vapor, water molecules become available for the formation of hydrates, when required for stable polymorphs.

Once the organizational and/or water absorbing process starts at the surface, it is possible that the crystallization process gradually spreads into the interior of the particle without the need for contact with or dissolution within the solvent.

If this is correct there are two facts which seem to indicate that these microcondensations or molecular agglomerations are extremely minute. First, if enough solvent condensation occurred on the surface of the particle, the solvent would at least partially dissolve it and modify its shape. To avoid any partial dissolution, the amounts deposited by the vapor must be extremely minute.

Second, during exposure to solvent vapors the particles, because of their small size and large quantity, inevitably come to contact with one another. Were there to be any surface dissolution of the particles, as would occur if the substantial quantities of amounts of deposited vapor were not very minute, the particles would tend to stick to each other and form lumps or agglomerates. Under the conditions described herein, this does not occur.

EXAMPLES

The following examples illustrate how a substance or mixtures of substances are transformed from metastable to more stable crystalline structures according to the method of the present invention.

Example 1

Microsheres of 17β Estradiol.

This and other substances were melt/sprayed into droplets and later congealed into microspheres to be suspended in a water medium for extended release injectables.

Microspheres of 17β estradiol obtained after congealing their sprayed droplets at −50° C. showed a high proportion of amorphous matter Heating these microspheres sufficiently allowed the amorphous matter to crystallize into an anhydrous polymorph. However, despite being fully crystallized, these microspheres remained stable at room temperature but unstable when placed in water, due to the fact that the stable polymorph is a hemihydrate (Salole, The Physicochemical Properties of Estradiol, J.-Pharm-Biomed-Anal., 1987:5 (7), 635-648; Jeslev et al., Organic Phase Analysis, II. Two unexpected cases of pseudopolymorphism, Arch. Pharm. Chemi. Sci. Ed., 1981, 9, 123- 130). Thus, in aqueous solution, the substance spontaneously reverted to this more stable polymorph and in so doing restructured its crystalline arrangement into shapes which differed from the microsphere.

When these microspheres were placed in a recipient of approximately 7 liters and exposed for 24 hours at 20–25° C. to the vapors of 13.5 mL of a (50—50) mixture of ethanol and water kept in a porous cellulose material, the initially amorphous microspheres crystallized directly in the presence of the vapors into the stable hemihydrate polymorph and were thereafter stable when placed in water.

To evaluate the stability of the crystallized 17β Estradiol microspheres, the microspheres were placed in aqueous solution at 40° C. and observed by optical microscopy after 274 days. Thus, the stability in water of the microspheres containing the hemihydrate form may be verified using optical microscopy.

The residual ethanol present in the microspheres was less than 0.01%.

Example 2

Testosterone Microspheres

Several authors have reported that testosterone has several polymorphs, of which two hydrate forms are stable in water (Frokjaer et al., Application of Differential Scanning Calorimetry to the Determination of the Solubility of a Metastable Drug, Arch. Pharm. Chemi. Sci. Ed., 2, 1974, 50–59; Frokjaer et al., Dissolution Behavior Involving Simultaneous Phase Changes of Metastable Drugs, Arch. Pharm. Chemi. Sci. Ed., 2, 1974, 79–54; Thakkar et al., Micellar Solubilization of Testosterone III. Dissolution Behavior of Testosterone in Aqueous Solutions of Selected Surfactants, J. Pharm. Sci., Vol 58, No. 1, 68–71).

Testosterone microspheres, immediately after being produced by the same spray/congealing as for 17β estradiol, showed an equally high amorphous content. Heating the microspheres at 117° C. for 23 hours crystallized them into an anhydrous polymorph similar to that found in the commercial raw material. However, when these microspheres were placed in water, the anhydrous polymorph spontaneously converted into a hydrated structure, a conversion that caused the microspheres to lose their shape.

In contrast, when these microspheres were placed in a recipient of approximately 7 liters and exposed for 24 hours at 20–25° C. to the vapors of 40 mL of a (80–20) mixture of acetone and water kept in a porous cellulose material, initially amorphous microspheres crystallized directly in the presence of the vapors into the stable hydrate polymorphs mentioned earlier. These crystalline particles exhibited storage stability when placed in water.

To evaluate the stability of the testosterone microspheres, the microspheres were placed in aqueous solution at 40° C. and visualized after 54 days by optical microscopy. For comparison, non-crystallized testosterone microspheres (melt-congealed only) were also placed in aqueous solution and visualized after 40 days. The stability in water of the microspheres containing the hydrate polymorphs versus the non-crystallized microspheres was apparent by comparing the optical microscopy photographs.

The residual ethanol present in the microspheres was less than 0.01%.

Example 3
Progesterone Microspheres

Progesterone microspheres, immediately after being produced by the same spray/congealing as for the previous substances, showed some crystallization in polymorphs I and II. No hydrate polymorphs have been reported for progesterone.

However, when the microspheres were placed in a recipient of approximately 7 liters and exposed for 4 hours at 20–25° C. to the vapors of 13.5 mL of a (50—50) mixture of ethanol and water kept in a porous cellulose material, the initially amorphous microspheres crystallized directly in the presence of the vapors into the stable polymorph I and were thereafter stable when placed in water.

To evaluate the stability of the crystallized Progesterone microspheres, the microspheres were placed in aqueous solution at 40° C. and observed by optical microscropy after 187 days.

It should also be noted that in the case of progesterone, the use of solvent vapors also provoked the conversion of polymorph II, present in the mixture of structures found after spray-congealing, into polymorph I, as observed by DSC.

In addition, in the case of progesterone, the exposition to solvent vapors was also successfully obtained with a mobile system. The microspheres were placed in a 1.6 liter hermetic crystallizing chamber turning at 5 RPM and placed in contact with ethanol vapors for 24 hours.

In both experiments the residual ethanol present in the microspheres was less than 0.01%.

Example 4
Astemizole Microspheres

To demonstrate that the method of the present invention was successful in forming stable crystals of organic compounds other than steroids and sterols, astemizole microspheres were subjected to the solvent vapor treatment.

Immediately after being produced by the same spray/congealing as for the previous substances, astemizole microspheres also showed a high amorphous content. However, when 100 mg microspheres were placed in a recipient of approximately 0.5 liters and exposed for 24 hours at 30° C., to the vapors of 0.5 mL of ethyl acetate kept in a porous cellulose material, the initially amorphous microspheres crystallized directly in the presence of the vapors into a stable polymorph. Similar results were obtained in another experiment by using acetone.

To evaluate stability of the astemizole microspheres, the microspheres were placed in aqueous solution at 40° C. and observed by optical microscopy after 76 days.

Example 5
Astemizole Pellets

In the case of astemizole pellets, immediately after congealing the molten raw material at −50° C. the pellets showed a high content of amorphous material. However, the exposure of 150 mg of astemizole pellets in a recipient of approximately 0.5 L for 24 hours at 30° C. to the vapors of ethyl acetate contained in a porous cellulose material led to crystallization of the pellets without any modification on the particle shape. Similar results were obtained by using acetone in another experiment.

Example 6
Cholesterol Microspheres

Immediately after being produced by the same spray/congealing as for the previous substances, cholesterol microspheres showed amorphous content. No polymorphs have been reported for cholesterol.

When 100 mg of the microspheres were placed in a recipient of approximately 0.5 liters and exposed for 8 hours at 30° C. to the vapors of 1 mL of acetic acid kept in a porous cellulose material, the initially amorphous microspheres crystallized completely.

Crystallization of Mixtures of Substances

Mixing different substances in melt congealed shaped particles of ingredients can provide important advantages. Amongst them are: modulating the dissolution rates, lowering the melting point, diluting the active ingredients, improving the chemical stability of main ingredients, etc. Thus, the ability to crystallize particles composed of mixtures of substances increases very importantly the range of applications of melt congealed solids in health and other areas.

Many mixtures of substances can be melted and congealed. However, because of the different physical characteristics of each component, such mixtures tend to form complex metastable structures on congealing and, with the exception of eutectic mixtures, it is impossible to crystallize them because one of the substances can melt before reaching the transition-point temperature.

As above, particles comprising pluralities of allotropic organic compounds are likewise suitable for the solid state crystallization of the present invention. The crystallization is complete and the resulting particles are stable in both water and dry environments at the usual temperatures of storage and use.

Example 7
Microspheres of a Mixture of 40% 17β Estradiol and 60% Cholesterol.

The microspheres of this mixture were obtained by melting together the components and, as for the pure substances, sprayed into droplets and congealed into microspheres. They initially showed a high amorphous content.

When the microspheres were placed in a recipient of approximately 7 liters and exposed for 24 hours at 30° C. to the vapors of 8 mL of ethanol kept in a porous cellulose material, the initially amorphous microspheres crystallized completely in the presence of the vapors.

The microspheres were dried at 60° C. in a vacuum for 24 hours and residual ethanol present in the microspheres was less than 0.01%.

To evaluate the stability of the microspheres, non-crystallized microspheres (melt-congealed only) and microspheres according to the present invention were separately placed in aqueous solution at 40° C. and observed by optical microscopy after 82 days. As observed by optical microscopy, the microspheres crystallized according to the present invention remained stable over time when placed in water, whereas the non-crystallized microspheres did not.

Stability in Vivo

In the case of slow release injected or implanted medicinal drugs, the physical integrity of the particles after their administration to the patient is essential to assure the desired rates of delivery and the reproducibility of effect. Thus, the stability in vivo of the microspheres described in the previous example was checked in New Zealand male rabbits. optical microscopy photographs taken 1, 4, 7 and 14 days after intramuscular injection showed that the microspheres remain whole, until they have finally dissolved. For comparison, microspheres that had not been crystallized were also injected. Their optical microscopy photographs showed that these microspheres changed into non-spherical shapes.

Example 8
Microsphrers of a Mixture of 10% 17β Estradiol & 90% Cholesterol.

As for the previous example, the microspheres of this mixture were obtained by melting together the components, sprayed into droplets and congealed into microspheres. Initially, they showed a high amorphous content.

When the microspheres were placed in a recipient of approximately 7.0 liters and exposed for 24 hours at 5° C., to the vapors of 8 mL of ethanol kept in a porous cellulose material, the initially amorphous microspheres crystallized completely in the presence of the vapors.

The microspheres were later dried at 60° C. in a vacuum for 24 hours and the residual ethanol present in the microspheres was less than 0.01%.

To evaluate stability of the crystallized microspheres, they were placed in aqueous solution at 40° C. and observed by optical microscopy after 141 days.

Example 9
Microspheres of a Mixture of 95.2% Progesterone & 4.8% 17β Estradiol.

As for the previous examples the microspheres of this mixture were obtained by melting together the components, sprayed into droplets and congealed into microspheres. Initially, they showed a high amorphous content.

When the microspheres were placed in a recipient of approximately 7 liters and exposed for 24 hours at 20–25° C. to the vapors of 2 mL of ethanol kept in a porous cellulose material, the initially amorphous microspheres crystallized completely in the presence of the vapors.

The microspheres were later dried at 60° C. in a vacuum for 24 hours and the residual ethanol present in the microspheres was less than 0.01%.

Example 10
Microspheres of a Mixture of 60% Progesterone & 40% Cholesterol.

As for the previous examples the microspheres of this mixture were obtained by melting together the components, sprayed into droplets and congealed into microspheres. They initially showed a high amorphous content.

When the microspheres were placed in a recipient of approximately 7 liters and exposed for 24 hours at 30° C. to the vapors of 2 mL of ethanol kept in a porous cellulose material, the initially amorphous microspheres crystallized completely in the presence of the vapors.

The microspheres were later dried at 60° C. in a vacuum for 24 hours and the residual ethanol present in the microspheres was less than 0.01%.

Thus, it is clear that the method of the present invention is widely applicable in forming stable, crystallized particles, microspheres and pellets of a variety of organic compounds and mixtures that maintain their shape in aqueous solution. Hence, the present method should find significant utility in the manufacture of pharmaceuticals and pharmaceutical compositions, particularly where treatment calls for administration of the pharmaceutical in a slow release formulation.

While some embodiments of the present invention have been shown or described herein, it will be apparent to those skilled in the art that various modifications may be made to the crystallization process without departing from the spirit and scope of the present invention.

What is claimed is:

1. A plurality of storage stable particles of uniform shape consisting essentially of a plurality of allotropic organic compounds, wherein each of said allotropic organic compounds consists of a uniform crystalline character and a plurality of crystalline domains; said organic compounds retaining said crystalline character, and said particles retaining said uniform shape on storage in aqueous media for at least about one month.

2. The particles of claim 1, wherein the uniform shape of the particles is selected from the group consisting of sphere, spheroid, and cylinder.

3. The particles of claim 1, wherein the particles are in the shape of a sphere of diameter of between about 1 and about 1,000 microns.

4. The particles of claim 1, wherein the particles are in the shape of a sphere of diameter of between about 10 and about 300 microns.

5. The particles of claim 1, wherein the desired crystalline form of at least one of said allotropic organic compounds is a hydrate.

6. The particles of claim 1, wherein at least one of said allotropic organic compounds is a steroid or sterol.

7. The particles of claim 6, wherein said steroid or sterol is selected from the group consisting of 17 β-estradiol, estrogen, testosterone, progesterone, cholesterol, and mixtures thereof.

8. The particles of claim 1, wherein at least one of said allotropic organic compounds is astemizole, cisapride or oxatomide.

9. The particles of claim 1, wherein said particles are in the shape of a cylinder of length of about 1,000 to 5,000 microns and a diameter of about 500 to 1,000 microns.

10. The particles of claim 1, wherein one or more of said compounds is a steroid or sterol, and one or more of said compounds is selected from the group consisting of oxatomide, nifedipine, astemizole, and cisapride.

11. The particles of claim 1, wherein one of said allotropic organic compounds is cholesterol.

\* \* \* \* \*